(12) United States Patent
Chen et al.

(10) Patent No.: US 11,054,410 B2
(45) Date of Patent: Jul. 6, 2021

(54) METHOD AND APPARATUS FOR IMPROVING USABILITY AND ACCURACY FOR PHYSIOLOGICAL MEASUREMENT ON MOBILE DEVICE

(71) Applicant: IXENSOR CO., LTD., Tpe (TW)

(72) Inventors: Yenyu Chen, Tpe (TW); Tungmeng Tsai, Tpe (TW); Chieh Hsiao Chen, Tpe (TW); Yaoching Tsai, Tpe (TW); Tangan Liu, Tpe (TW)

(73) Assignee: IXENSOR CO., LTD.

( * ) Notice: Subject to any disclaimer, the term of this patent is extended or adjusted under 35 U.S.C. 154(b) by 292 days.

(21) Appl. No.: 15/739,157

(22) PCT Filed: Sep. 14, 2016

(86) PCT No.: PCT/CN2016/098971
§ 371 (c)(1),
(2) Date: Dec. 21, 2017

(87) PCT Pub. No.: WO2017/045601
PCT Pub. Date: Mar. 23, 2017

(65) Prior Publication Data
US 2018/0372714 A1 Dec. 27, 2018

Related U.S. Application Data

(60) Provisional application No. 62/219,383, filed on Sep. 16, 2015, provisional application No. 62/245,623, filed on Oct. 23, 2015.

(51) Int. Cl.
*G01N 33/487* (2006.01)
*G01N 27/327* (2006.01)
(Continued)

(52) U.S. Cl.
CPC ... *G01N 33/48785* (2013.01); *A61B 5/14532* (2013.01); *G01N 21/8483* (2013.01);
(Continued)

(58) Field of Classification Search
CPC ......... G01N 33/48785; G01N 21/8483; G01N 33/50; G01N 27/3273; G01N 2201/0221;
(Continued)

(56) References Cited

U.S. PATENT DOCUMENTS

2006/0222567 A1 10/2006 Kloepfer et al.
2009/0322341 A1 12/2009 Kraft et al.
(Continued)

FOREIGN PATENT DOCUMENTS

CN 1828301 A 9/2006
CN 202149891 U 2/2012
(Continued)

OTHER PUBLICATIONS

Preechaburan13 Surface Resonance Chemical Sensing on Cell Phones—Angewandte Chemie—2012 (Year: 2012).*
(Continued)

*Primary Examiner* — Benjamin R Whatley
*Assistant Examiner* — Jean Caraballo-Leon
(74) *Attorney, Agent, or Firm* — Su IP Consulting

(57) ABSTRACT

An accessory (800) is provided for a mobile device (102) to measure characteristics of a test strip (808). The accessory (800) includes a test strip adapter (806), a phone adapter (802), and a coupler (804). The test strip adapter (806) includes a test strip attachment for a test strip type and a first interlock shared with other test strip adapters for other test strip types. The phone adapter (802) includes a phone attachment for a mobile device model and a second interlock shared with other phone adapters for other mobile device models. The coupler (804) includes a third interlock that
(Continued)

forms a first mating pair with the first interlock of the test strip adapter (806), and a fourth interlock that forms a second mating pair with the second interlock of the phone adapter (802).

22 Claims, 15 Drawing Sheets

(51) Int. Cl.
*H04M 1/21* (2006.01)
*G01N 33/50* (2006.01)
*A61B 5/145* (2006.01)
*G01N 21/84* (2006.01)

(52) U.S. Cl.
CPC ......... *G01N 27/3273* (2013.01); *G01N 33/50* (2013.01); *H04M 1/21* (2013.01); *A61B 2562/0295* (2013.01); *G01N 2201/0221* (2013.01)

(58) Field of Classification Search
CPC ....... A61B 5/14532; A61B 2562/0295; H04M 1/21
See application file for complete search history.

(56) References Cited

U.S. PATENT DOCUMENTS

| | | |
|---|---|---|
| 2012/0244624 A1 | 9/2012 | Hsiao |
| 2013/0273528 A1 | 10/2013 | Ehrenkranz |
| 2014/0072189 A1* | 3/2014 | Jena ................. A61B 5/150358 382/128 |
| 2014/0120563 A1 | 5/2014 | Ozcan et al. |
| 2014/0170757 A1* | 6/2014 | Tsai ....................... G01N 21/78 436/55 |
| 2014/0296112 A1 | 10/2014 | O'Driscoll et al. |
| 2014/0362283 A1 | 12/2014 | Coppage et al. |
| 2015/0031412 A1* | 1/2015 | Quilter ................. A61B 5/0013 455/556.1 |
| 2015/0177147 A1 | 6/2015 | Mangan et al. |

FOREIGN PATENT DOCUMENTS

| | | |
|---|---|---|
| CN | 103002795 A | 3/2013 |
| CN | 203299206 U | 11/2013 |
| CN | 203445930 U | 2/2014 |
| CN | 104569379 A | 4/2015 |
| CN | 204479478 U | 7/2015 |
| JP | 2014532869 A1 | 12/2014 |
| KR | 10-2012-0109961 A | 10/2012 |
| KR | 10-2014-0127766 A | 11/2014 |
| KR | 101533343 B1 | 7/2015 |
| WO | 2014094442 A1 | 6/2014 |

OTHER PUBLICATIONS

Definition—Lexico—Over (Year: 2020).*
The Extended European Search Report, Application No. 16845715.8, dated Jul. 19, 2019.
International Search Report and Written Opinion of the International Searching Authority, International application No. PCT/CN2016/098971, dated Dec. 1, 2016.

* cited by examiner

US 11,054,410 B2

METHOD AND APPARATUS FOR IMPROVING USABILITY AND ACCURACY FOR PHYSIOLOGICAL MEASUREMENT ON MOBILE DEVICE

CROSS-REFERENCE TO RELATED APPLICATIONS

The present application is a U.S. national stage filing under 35 U.S. C. § 371 of International Application No. PCT/CN2016/098971, filed Sep. 14, 2016, which claims the benefit of U.S. Provisional Application No. 62/219,383 filed Sep. 16, 2015, and U.S. Provisional Application No. 62/245,623, filed Oct. 23, 2015. The International Application and the two U.S. Provisional Applications are incorporated by reference in their entirety.

FIELD

The present disclosure generally relates to methods and systems for optochemistry-based in-vitro diagnosis devices.

BACKGROUND

In recent years, in-vitro diagnosis (IVD) devices, especially blood glucose meters, have gained wide adoption among patients with chronic diseases. In order to take measurements, patients usually have to carry standalone IVD devices with them all day long. From time to time, patients forget to carry their IVD devices and are not able to monitor their health status in a timely manner.

For typical IVD measurements, test strips consisting enzyme and reagent are used. Upon receiving the sample fluid, the test strip's characteristics, such as electrical impedance or color, change according to the concentration of the targeted analyte, such as blood glucose or blood cholesterol.

Optochemistry-based IVD systems usually comprises test strips that change color according to the concentration of analyte received, specific light sources that illuminate on strips, optical sensors that detect scattering light, and light-isolating cases.

SUMMARY

In examples of the present disclosure, an accessory is provided for a mobile device to measure characteristics of a test strip. The accessory includes a test strip adapter, a phone adapter, and a coupler. The test strip adapter includes a test strip attachment for a test strip type and a first interlock shared with other test strip adapters for other test strip types. The phone adapter includes a phone attachment for a mobile device model and a second interlock shared with other phone adapters for other mobile device models. The coupler includes a third interlock that forms a first mating pair with the first interlock of the test strip adapter, and a fourth interlock that forms a second mating pair with the second interlock of the phone adapter.

BRIEF DESCRIPTION OF THE DRAWINGS

The foregoing and other features of the present disclosure will become more fully apparent from the following description and appended claims, taken in conjunction with the accompanying drawings. These drawings depict only several embodiments in accordance with the disclosure and are therefore not to be considered limiting of its scope. The disclosure will be described with additional specificity and detail through use of the accompanying drawings.

FIG. 5-1 show the details of a test strip device of FIG. 1 in examples of the present disclosure.

FIGS. 5-2 and 5-3 show the details of a test strip adapter compatible with the phone adapter of FIG. 1 from different angles in examples of the present disclosure.

FIG. 13-1 shows a mobile device accessory in examples of the present disclosure.

FIG. 13-2 shows a cover of FIG. 13-1 in examples of the present disclosure.

FIGS. 14-1 and 14-2 show a test strip adapter compatible with a coupler of FIG. 13 from different angles in examples of the present disclosure.

FIGS. 16-1 and 16-2 show the details of a test strip adapter of FIG. 15 from different angles in examples of the present disclosure.

FIG. 16-3 shows the details of a test strip adapter compatible with the coupler of FIG. 15 in examples of the present disclosure.

FIGS. 17-1 and 17-2 show the details of a coupler of FIG. 15 from different angles in examples of the present disclosure.

DETAILED DESCRIPTION

As used herein, the term "includes" means includes but not limited to, the term "including" means including but not limited to. The terms "a" and "an" are intended to denote at least one of a particular element. The term "based on" means based at least in part on. The term "or" is used to refer to a nonexclusive such that "A or B" includes "A but not B," "B but not A," and "A and B" unless otherwise indicated.

Today, most mobile devices include at least a display panel, which can serve as a light source for illumination. Besides, it also has at least one image or light sensor that locate at the same side of the display panel.

In the present disclosure, a test strip or a test strip device containing the test strip, along with the display panel and the image/light sensor of mobile devices (e.g., smartphone or tablet), are used to measure physiological biochemical parameter(s). Software in mobile device will instruct a user to complete the measurement procedure.

Positioning of the test strip or test strip device is important for getting an accurate value. Examples of the present disclosure provide methods to improve the compatibility and position accuracy of test device to mobile device (mobile phone or tablet). For simply, a mobile phone 102 is used as an example but the present disclosure is equally applicable to a tablet or other mobile devices.

Figure 1:
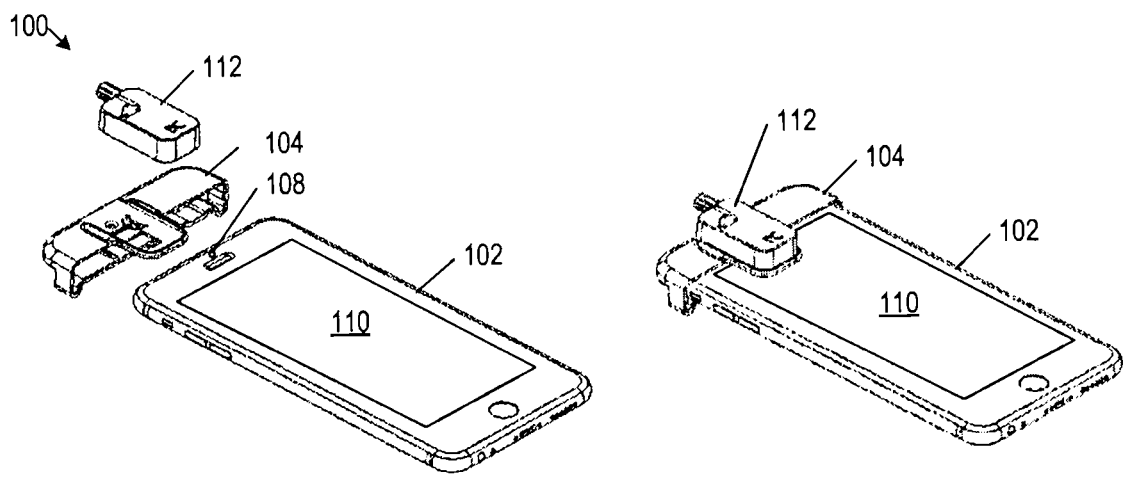
FIG. 1 shows a mobile device accessory in examples of the present disclosure.

FIG. 1 shows an accessory 100 for a mobile device 102 (e.g., mobile phone) in some examples of the present disclosure. Using accessory 100 and software, mobile phone 102 is able to measure a characteristic of a test strip and correlate the characteristic to health information.

Accessory 100 includes a phone adapter 104. Phone adapter 104 may be a removable clip that slides on and secures to the top of mobile phone 102. After clip 104 is secured to mobile phone 102, a test strip device 112 is placed on the clip. Test strip device 112 may be a single-use test strip carrier containing a test strip (as shown), a test strip adapter (described later) for a test strip, or a coupler (describe later) for joining clip 104 and the test strip adapter.

Figure 2:
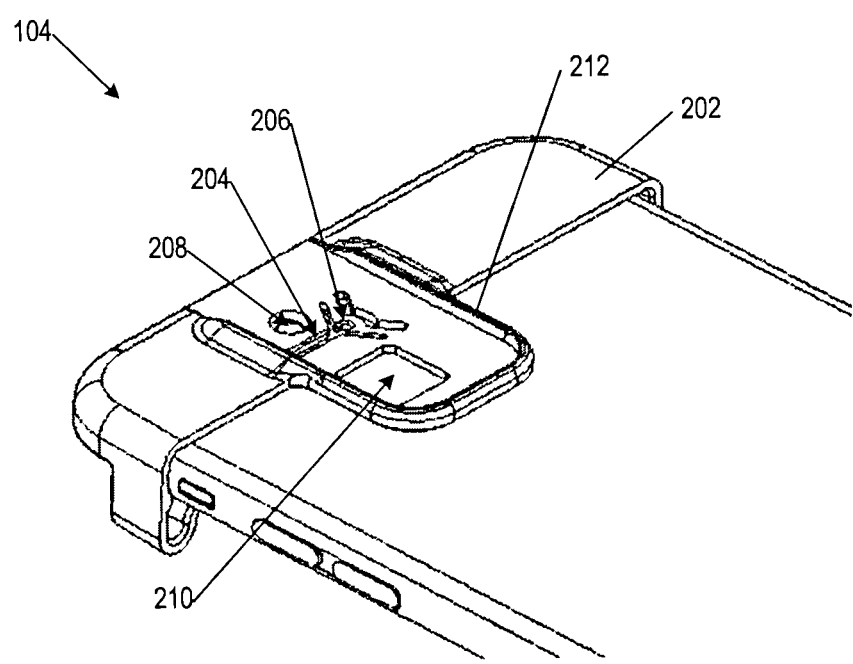
FIGS. 2, 3, and 4 show the details of a phone adapter of FIG. 1 in examples of the present disclosure.

FIG. 2 shows an enlarged view of clip 104 in some examples of the present disclosure. Clip 104 includes a faceplate 202 that defines a receiver slot 204. Faceplate defines a receiver slot 204 that receives protrusions or anchors that position test strip device 112 on the faceplate. The anchors may be similar to anchors 513 of test strip device carrier 500-1 in FIG. 5-1. Faceplate 202 includes V-shaped cutouts 206 that allows receiver slot 204 to flex when test strip device 112 is mounted or dismounted.

Faceplate 202 defines a camera window 208. When clip 104 is attached to mobile phone 102, camera window 208 exposes a camera 108 (FIG. 1) of mobile phone 102 so the camera can take pictures. Camera window 208 may include a lens. If faceplate 202 extends over a screen 110 (FIG. 1) of mobile phone 102, the faceplate defines a screen opening 210 that exposes a portion of the screen used as a light source.

To position test strip device 112 (FIG. 1) relative to clip 104 and mobile phone 102, faceplate 202 includes a guide 212. Guide 212 may be a frame that matches the footprint of test strip device 112. For example, guide 212 is a U-shaped frame with an open top end that receives test strip device 112. Alternatively, frame 212 may have other shapes, such as an L-shape.

Figure 3:
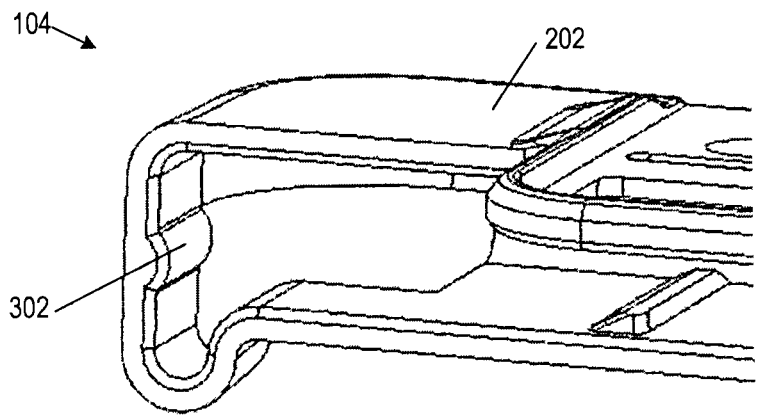

FIG. 3 shows the interior of clip 104 in some examples of the present disclosure. The inner side surfaces of clip 104 have retention features 302 (only one is visible) that press against the two sides of mobile phone 102 (FIG. 1). Retention features 302 may be protrusions arranged longitudinally along the insertion direction of mobile phone 102. Clip 104 may define a groove that accommodates a button of mobile phone 102.

Figure 4:
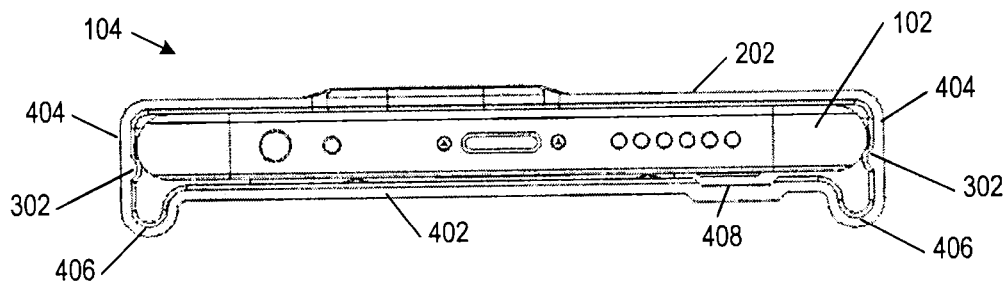

FIG. 4 shows clip 104 viewed from below in some examples of the present disclosure. Clip 104 includes faceplate 202, a backplate 402, and two sidewalls 404 joined to the sides of the faceplate and the backplate. Each sidewall 404 includes a U-shaped spring 406 that allows clip 104 to accommodate a range of mobile phone thicknesses. Backplate 402 includes a protrusion 408 to accommodate a back-facing camera (not labeled) of mobile phone 102 (FIG. 1). Although not visible, clip 104 includes a roof joined to the tops of faceplate 202 and backplate 402. Faceplate 202, backplate 402, sidewalls 404, and the roof form a mechanical attachment to mobile phone 102.

Clip 104 is a phone adapter for a particular phone model (e.g., iPhone 6). Accordingly, clip 104 has certain dimensions and incorporates certain elements to accommodate that particular phone model. At the same time, guide 212 (FIG. 2) has common dimensions shared between phone adapters for different mobile phone models so the phone adapters are compatible with test strip device 112. Guide 212 may be standardized for use by multiple vendors/manufacturers.

Test strip device 112 has certain dimensions and incorporates certain elements to accommodate a particular test strip type. At the same time, test strip device 112 has uniform dimensions shared between test strip devices for different test strip types so the test strip devices are compatible with clip 104.

Figures 1, 5:
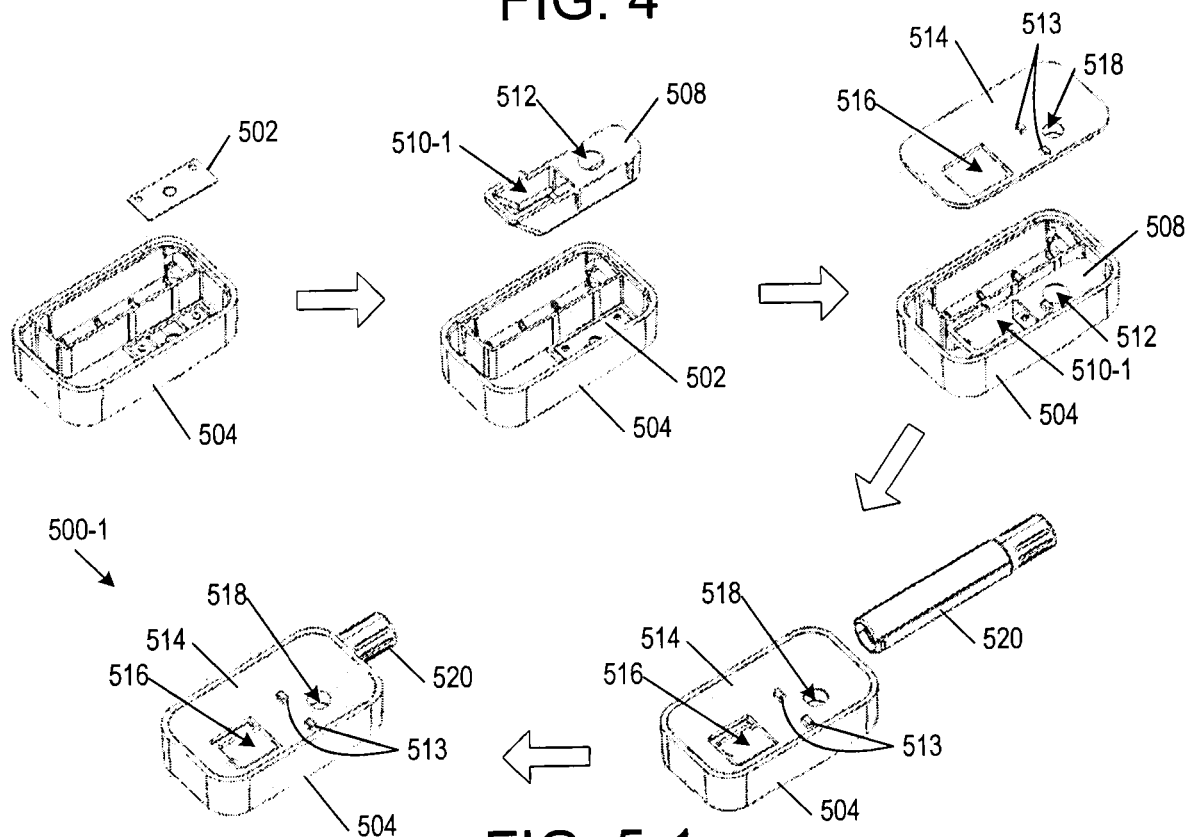
Figures 2, 5:
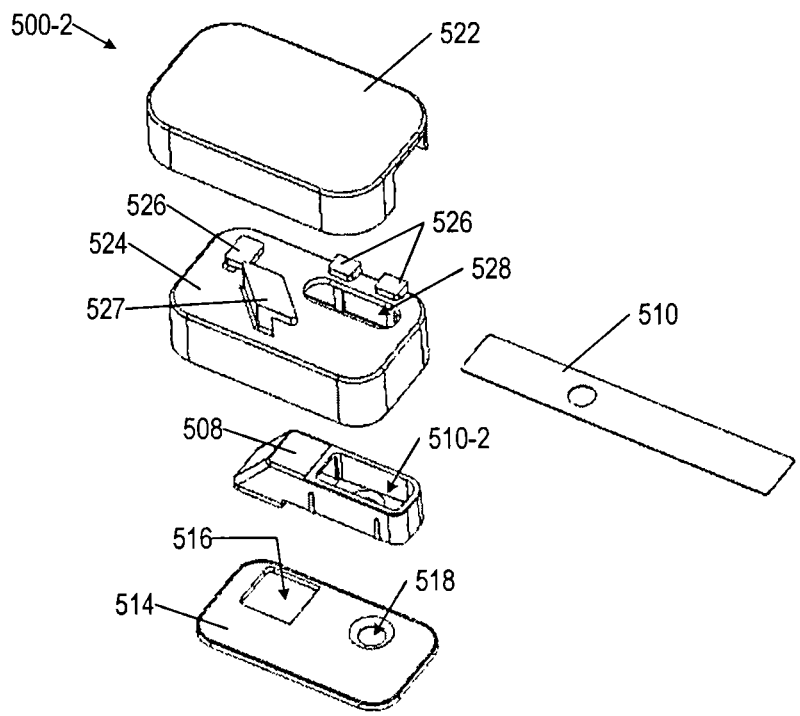
Figures 3, 5:
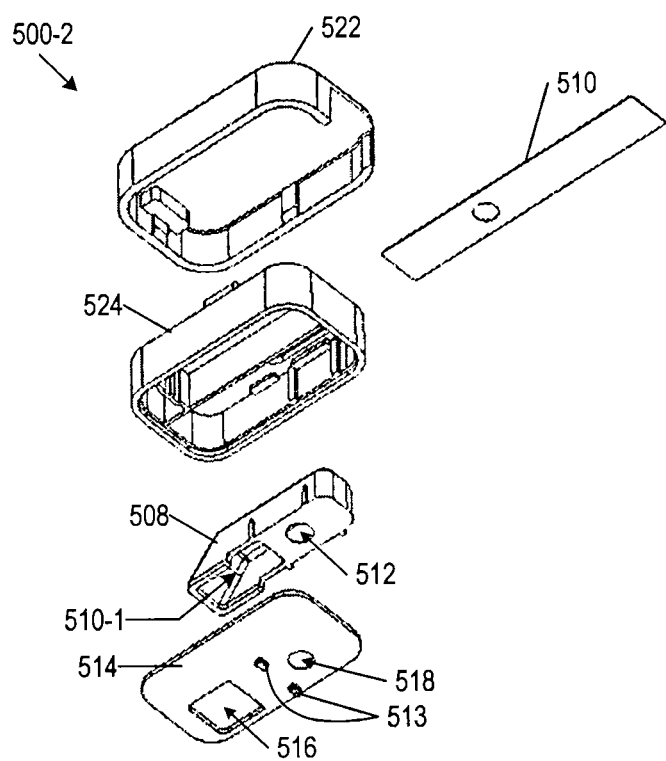

FIG. 5-1 shows the assembly a single-use test strip carrier 500-1 in some examples of the present disclosure. Test strip carrier 500-1 is a test strip device 112 compatible with clip 104. A test strip 502 is placed in and affixed to a carrier body 504 by adhesive or mechanical attachment. Carrier body 504 defines a sample collector that transports a physiological sample to test strip 502. A light guide 508 is placed over test strip 502 and fixed to carrier body 504 by adhesive or mechanical attachment. The bottom of light guide 508 includes an input port 510-1 and a camera hole 512. The top of light guide 508 includes an output port 510-2 (FIG. 5-2) that is in communication with input port 510-1 and camera hole 512. A carrier base 514 locks onto the open bottom of carrier body 504. Carrier base 514 defines a light hole 516 and a camera hole 518 over input port 510-1 and camera hole 512 of light guide 508, respectively. Carrier base 514 includes anchors 513 that fits into receiver slot 204 (FIG. 2) on faceplate 202 (FIG. 2). A lancet 520 is inserted into a lancet opening in carrier body 504.

In operation, a user provides a sample on sample collector, which transports the sample to test strip 502. Light guide 508 receives light from screen 110 (FIG. 1) through light hole 516 and input port 510-1, and projects the light out through output port 510-2 (FIG. 5-2) on a reaction area of test strip 510. Camera 108 (FIG. 1) captures an image of the reaction area through camera hole 518, camera hole 512, and output port 510-2.

In operation, a user provides a sample on sample collector 114, which transports the sample to test strip 502. Light guide 508 receives light from screen 110 (FIG. 1) through light hole 516 and input port 510-1, and projects the light out through output port 510-2 (FIG. 5-2) on a reaction area of test strip 510. Camera 108 (FIG. 1) captures an image of the reaction area through camera hole 518, camera hole 512, and output port 510-2.

FIGS. 5-2 and 5-3 show an exploded view of a test strip adapter 500-2 in examples of the present disclosure. Test strip adapter 500-2 is a test strip device 112 compatible with clip 104. Test strip adapter 500-2 includes a carrier cover 522, a carrier body 524, carrier base 514, and light guide 508.

Light guide 508 is placed in and affixed to carrier body 524 by adhesive or mechanical attachment, and carrier base 514 locks onto the open bottom of carrier body 524. As described before, carrier base 514 includes anchors 513 and defines light hole 516 and camera hole 518 over input port 510-1 (FIG. 5-1) and camera hole 512 (FIG. 5-1) of light guide 508, respectively.

Carrier body 524 has a top with guides 526 and defines a test strip opening 528. Guides 526 define a slot dimensioned to receive test strip 510. Carrier body 524 includes additional an additional guide 527 for compatibility with another test strip type. Test strip opening 528 is located within the space defined by guides 526 and over output port 510-2 of light guide 508.

In operation, a user provides a sample on test strip 510, insert the test strip into the slot defined by guides 526 and over test strip opening 528, and places carrier cover 522 onto carrier body 524 to block out ambient light. Light guide 508 receives light from screen 110 (FIG. 1) through light hole 516 and input port 510-1 (FIG. 5-1), and projects the light out through output port 510-2 and test strip opening 528 on a reaction area of test strip 510. Camera 108 (FIG. 1) captures an image of the reaction area through camera hole 518, camera hole 512 (FIG. 5-1), output port 510-2, and test strip opening 528.

Figure 6:
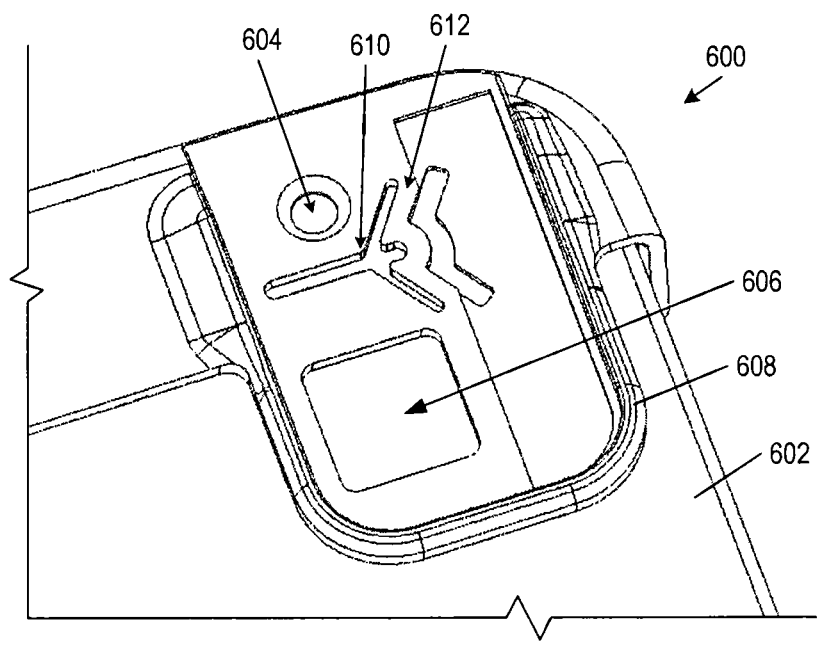
FIG. 6 shows a phone adapter compatible with the test strip device of FIG. 1 in examples of the present disclosure.

FIG. 6 shows a phone adapter 600 in some examples of the present disclosure. Phone adapter 600 is a removable clip similar to clip 104 (FIG. 1) but for a different phone model 602 (e.g., Galaxy S6). Clip 600 includes a camera window 604, a screen window 606, and a guide 608 located toward the side of the clip to match the location of the camera on this particular phone model. Clip 600 also includes an anchor slot 610 for receiving anchors on a test strip device, and cutouts 612 that allows anchor slots 610 to flex. Clip 600 may otherwise be similar to clip 104.

Figure 7:
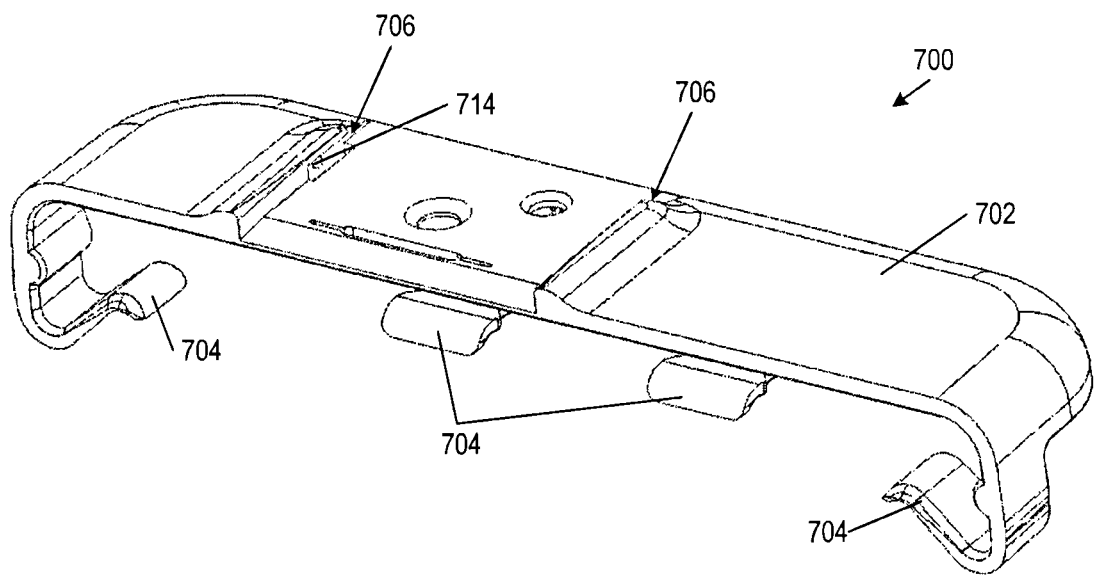
FIG. 7 shows a phone adapter compatible with the test strip device of FIG. 1 in examples of the present disclosure.

FIG. 7 shows a phone adapter 700 in some examples of the present disclosure. Phone adapter 700 is a removable clip similar to clip 104 (FIG. 1). Clip 700 includes a faceplate 702 and spring clips 704 that extend down from the top and the two sides of the faceplate to clamp onto the top end of mobile phone 102 (FIG. 1). Spring clips 704 form a mechanical attachment to mobile phone 102. Instead of spring clips 704, clip 700 may include sidewalls, a backplate, and a roof like clip 104.

Faceplate 702 includes a guide 706. Guide 706 may be an interlock that forms a mating pair with a corresponding an interlock on test strip device 112 (FIG. 1). For example, interlock 706 consists of slots or rails, and the counterpart interlock on test strip device 112 consists of tabs or way that slide in slots or rails 706. Each slot 706 includes a retention feature 714 that engages a counterpart retention feature on a corresponding tab on test strip device 112. For example, retention feature 714 is a detent catch or detent notch. Clip 700 may be similar to clip 104 in other manners.

Figure 8:
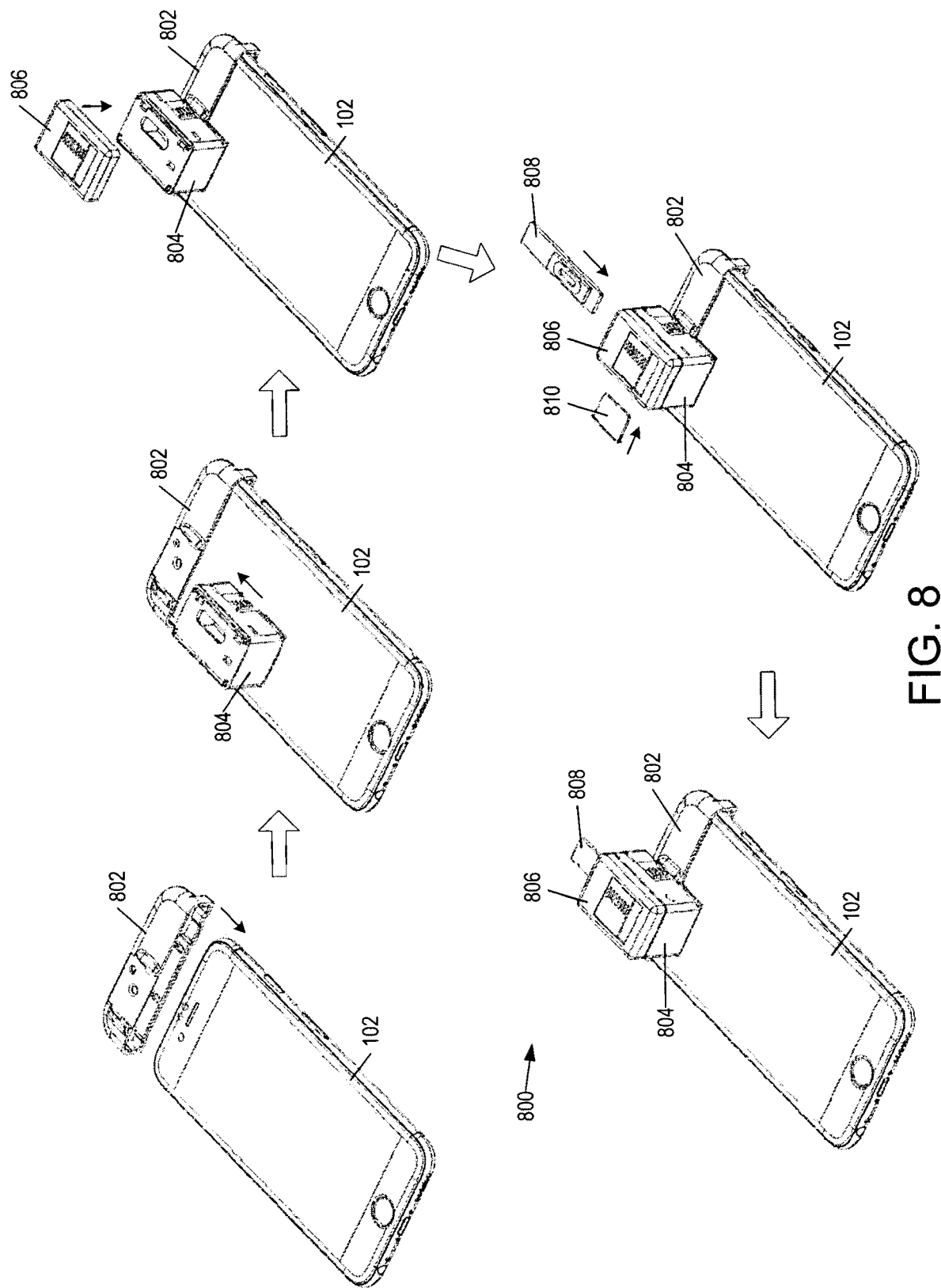
FIG. 8 shows a mobile device accessory in examples of the present disclosure.

FIG. 8 shows the assembly of an accessory 800 for mobile phone 102 in some examples of the present disclosure. Using accessory 800 and software, mobile phone 102 is able to measure a characteristic of a test strip and correlate the characteristic to health information.

Accessory 800 includes a phone adapter 802, a coupler 804, and a test strip adapter 806 in some of the present disclosure. Phone adapter 802 is configured for a particular phone model, test strip adapter 806 is configured for a particular test strip type, and coupler 804 provides a common interface between the phone adapter and the test strip adapter so phone adapters for different phone models may be used with test strip adapters for different test strip types. The coupler interface may be standardized for use by multiple vendors/manufacturers. Phone adapter 802 may be clip 700. As shown, clip 802 slides on and secures to the top of mobile phone 102, coupler 804 slides on and secures to the clip, and test strip adapter 806 mounts on the coupler. A test strip 808 and a code card 810 insert into slots in test strip adapter 806.

Figure 9:
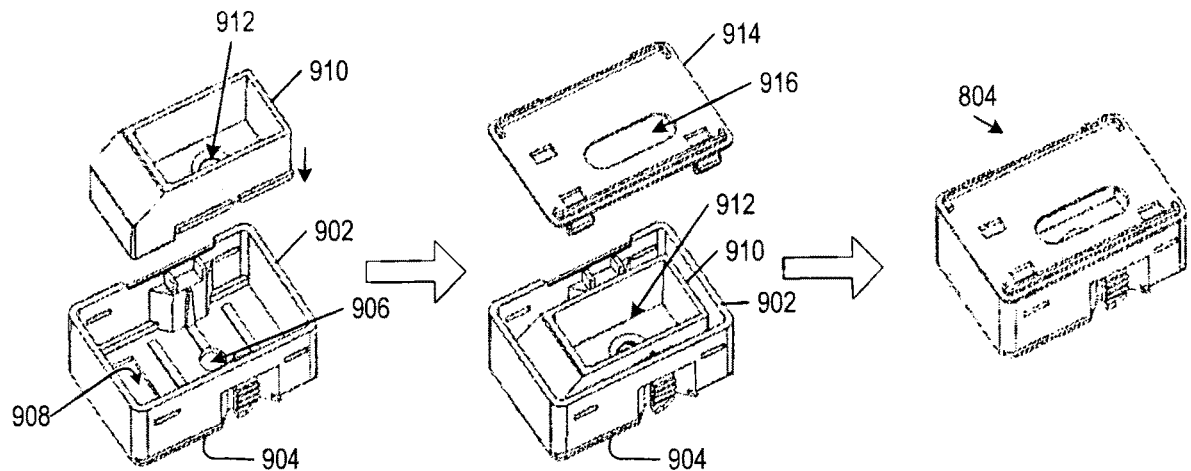
FIG. 9 shows the details of a coupler of FIG. 8 in examples of the present disclosure.

FIG. 9 shows the assembly of coupler 804 in some examples of the present disclosure. Coupler 804 includes a coupler body 902, a light guide 910, and a lid 914.

Coupler body 902 has a base 904 that defines a camera window 906 and a screen window 908. When coupler 804 is mounted on clip 802, camera window 906 is located over camera window 208 (FIG. 2) and camera 108 (FIG. 1), and screen window 908 is located over screen opening 210 (FIG. 2) and a portion of screen 110 (FIG. 1).

Light guide 910 is seated in and affixed to coupler body 902 by adhesive or mechanical attachment. Light guide 910 defines a hole, a space, or a combination of a hole and a space over camera window 906 of coupler body 902.

Lid 914 locks onto the open top of coupler body 902 to form a casing. Lid 914 defines a test strip opening 916 over hole or space 912 of light guide 910.

Figure 10:
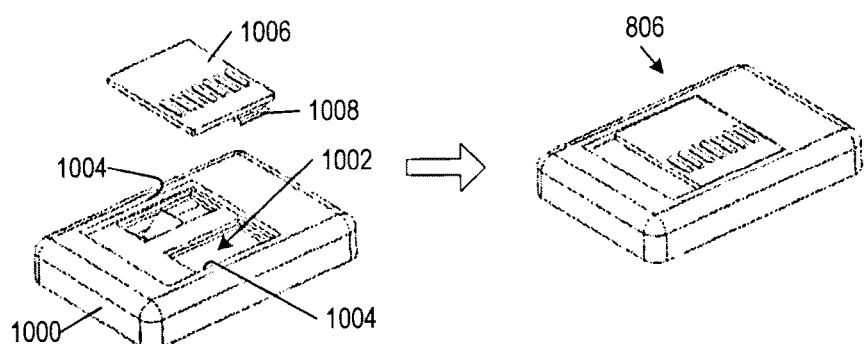
FIG. 10 shows the details of a test strip adapter of FIG. 8 in examples of the present disclosure.

FIG. 10 shows the assembly of test strip adapter 806 in some examples of the present disclosure. Test strip adapter 806 is a cover that has a cover body 1000 defining a test strip opening 1002. Cover body 1000 includes tracks 1004 along the two sides of test strip opening 1002. Cover 806 includes a sliding door 1006 having tabs 1008 that fit in tracks 1004 to allow it to slide between open and closed positions. When sliding door 1006 is open, a user can place a sample on test strip 808 located just below test strip opening 1002.

Figure 11:
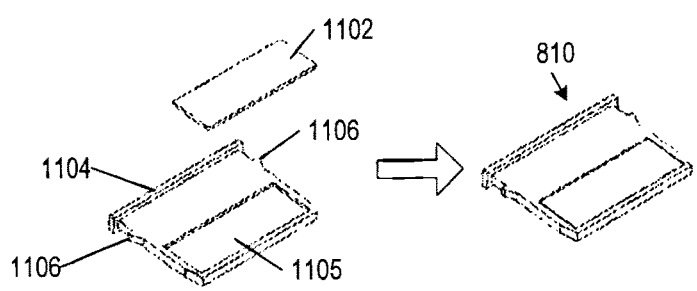
FIG. 11 shows a code card of FIG. 8 in examples of the present disclosure.

FIG. 11 shows code card 810 in some examples of the present disclosure. Code card 810 includes a code label 1102 and a label adapter 1104 defining a depression 1105 for seating the label. Label adapter 1104 includes retention features 1106 that lock onto counterpart retention features on the sides of the code card slot in cover 806 (FIG. 8).

Figure 12:
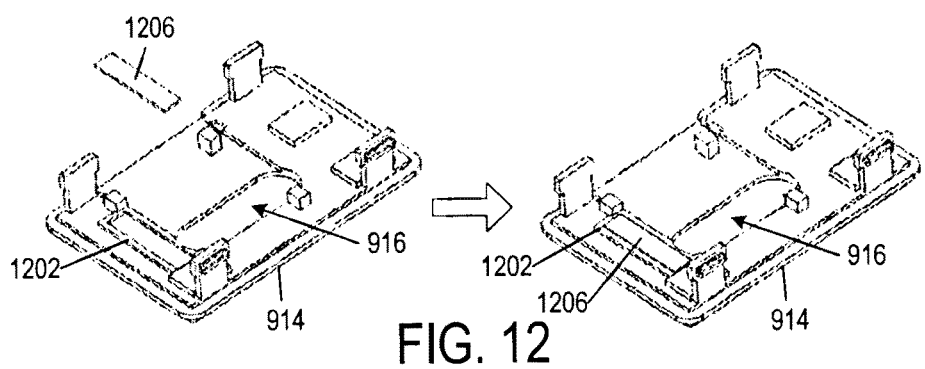
FIG. 12 shows the details of a lid for the coupler of FIG. 8 in examples of the present disclosure.

FIG. 12 shows the backside of lid 914 in examples of the present disclosure. The backside of lid 914 defines a frame 1202 adjacent to test strip opening 916 for affixing a temperature detection card 1206.

Figures 1, 13:
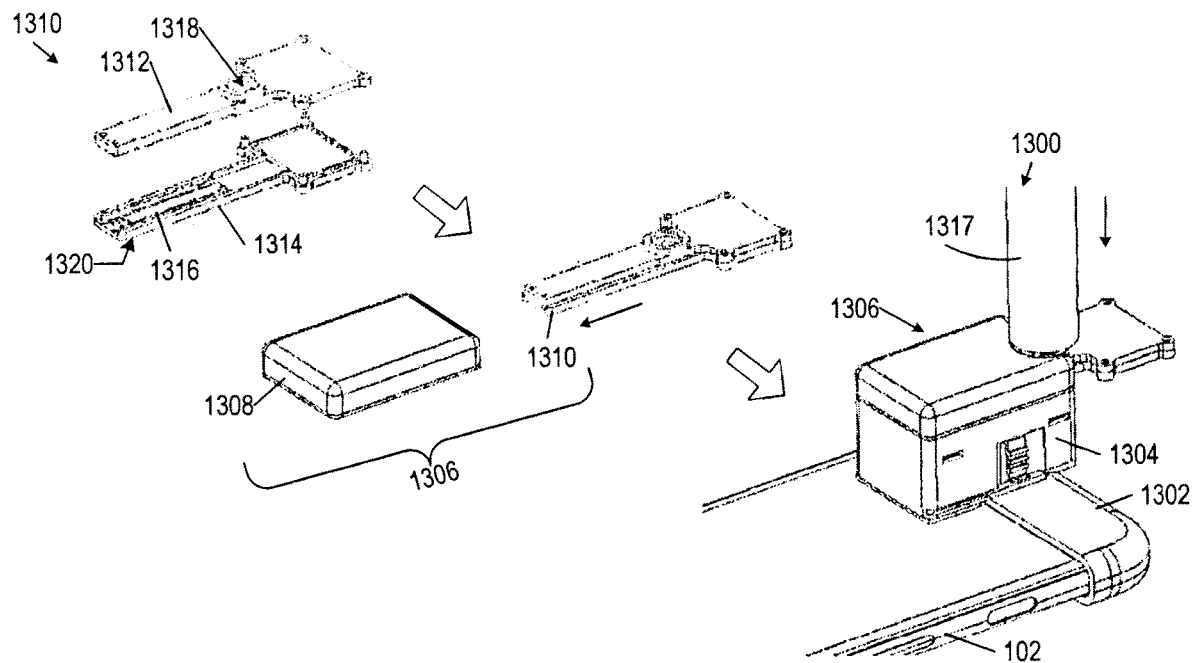
Figures 2, 13:
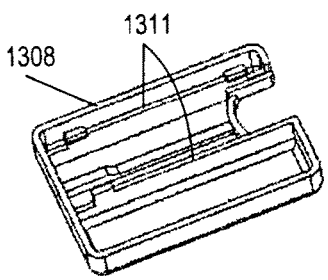

FIGS. 13-1 and 13-2 show the assembly of an accessory 1300 for mobile phone 102 in some examples of the present disclosure. Using accessory 1300 and software, mobile phone 102 is able to measure a characteristic of a test strip and correlate the characteristic to health information.

Accessory 1300 includes a phone adapter 1302, a coupler 1304, and a test strip adapter 1306 in some examples of the present disclosure. Phone adapter 1302 is configured for a particular phone model, test strip adapter 1306 is configured for a particular test strip type, and coupler 1304 provides a common interface between the phone adapter and the test strip adapter.

Phone adapter 1302 is a removable clip similar to clip 700. As shown, clip 1302 slides on and secures to the top of mobile phone 102, coupler 1304 slides on and secures to the clip, and test strip adapter 1306 mounts on the coupler. Test strip adapter 1306 includes an adapter cover 1308 and a test strip carrier 1310. Adapter cover 1308 has guides 1311 that define a slot to receive test strip carrier 1310. Test strip carrier 1310 includes a top half 1312 and a bottom half 1314. A test strip 1316 is seated in and affixed to bottom half 1314 by adhesive or mechanical attachment, and top half 1312 locks onto the bottom half. Top half 1312 defines a sample collector 1318 to transport a sample to test strip 1316. In some applications, a user deposits a sample in a tube 1317 with a solution (e.g., a buffer), mixes them, and inserts the tube into sample collector 1318 to provide a mixed solution to test strip 1316. Bottom half 1314 includes a test strip opening 1320 to view a reaction area on test strip 1316.

Figures 1, 2, 14:
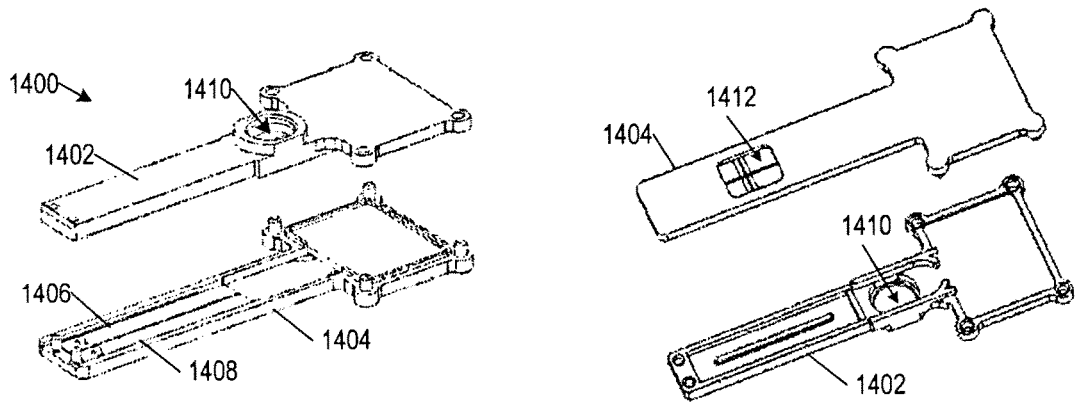

FIGS. 14-1 and 14-2 show a test strip carrier 1400 that is compatible with cover 1308 in some examples of the present disclosure. Test strip carrier 1400 is similar to test strip carrier 1310. Test strip carrier 1400 includes a top half 1402 and a bottom half 1404. Two different test strips 1406 and 1408 are seated in and affixed to bottom half 1404 by adhesive or mechanical attachment, and top half 1402 locks onto the bottom half. Top half 1402 defines a sample collector 1410 to transport a sample to test strips 1406 and 1408. Bottom half 1404 includes a test strip opening 1412 to view reaction areas on test strips 1406 and 1408.

Figure 15:
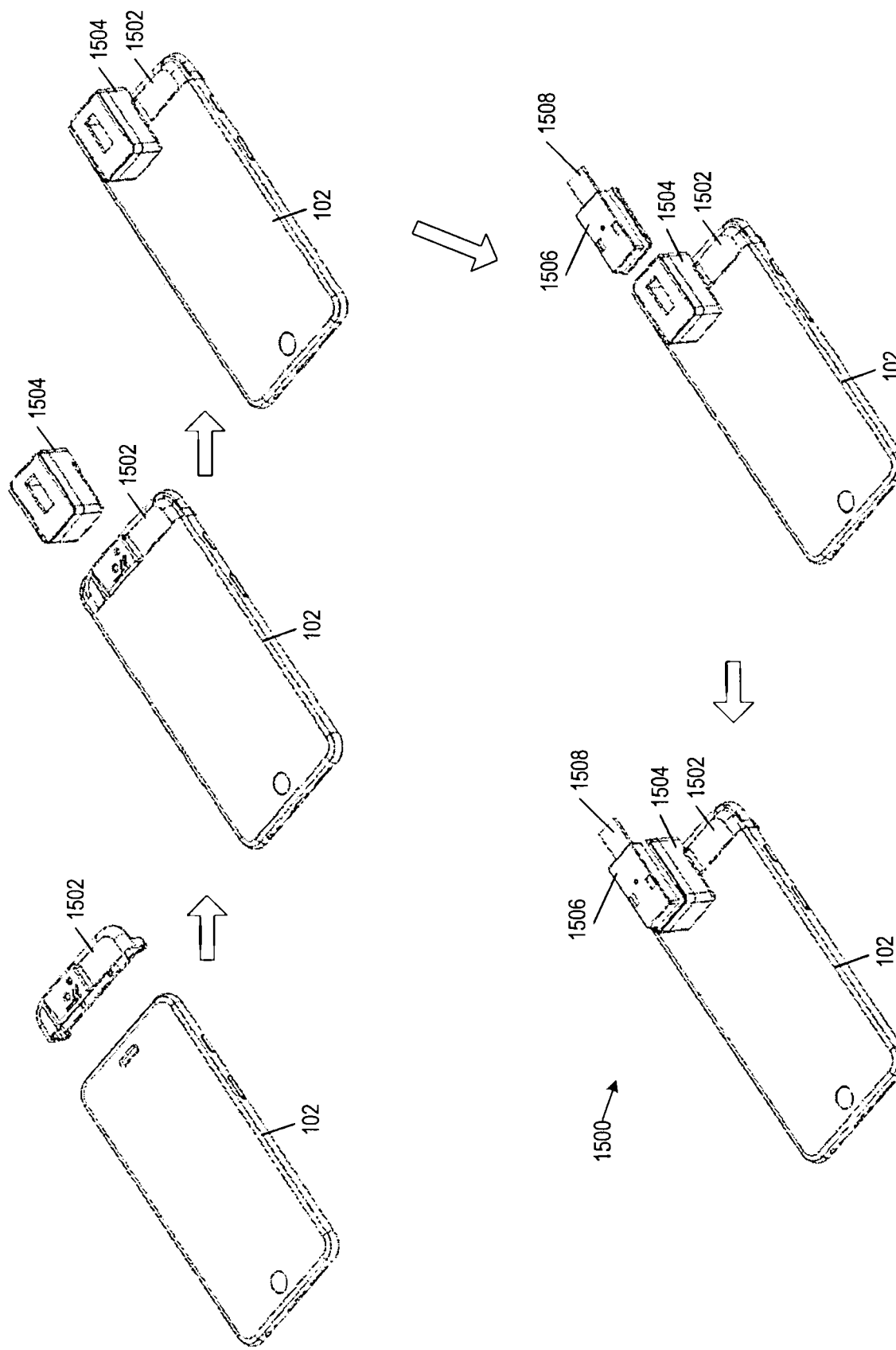
FIG. 15 shows a mobile device accessory in examples of the present disclosure.

FIG. 15 shows the assembly of an accessory 1500 for mobile phone 102 in some examples of the present disclosure. Using accessory 1500 and software, mobile phone 102 is able to measure a characteristic of a test strip and correlate the characteristic to health information.

Accessory 1500 includes a phone adapter 1502, a coupler 1504, and a test strip adapter 1506 in some examples of the present disclosure. Phone adapter 1502 is configured for a particular phone model (e.g., iPhone 6 from Apple), test strip adapter 1506 is configured for a particular test strip type, and coupler 1504 provides a common interface between the phone adapter and the test strip adapter. Phone adapter 1502 may be clip 700. As shown, clip 1502 slides on and secures to the top of mobile phone 102, coupler 1504 slides on and secures to the clip, test strip adapter 1506 mounts on a test strip 1508, and the test strip adapter slides on and secures to the coupler. Prior to mounting test strip adapter 1506 on test strip 1508, a user deposits a sample on the test strip.

Figures 1, 16:
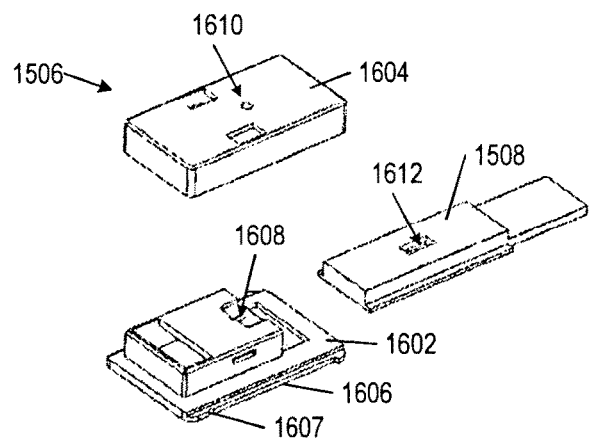
Figures 2, 16:
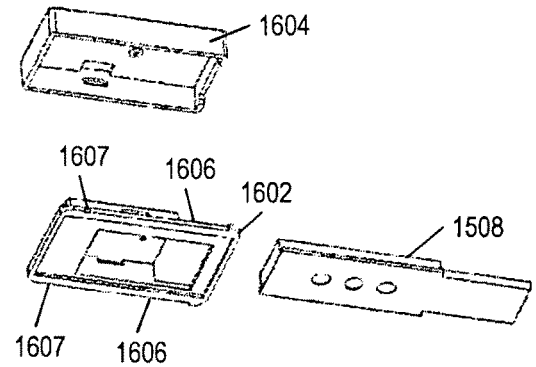
Figures 3, 16:
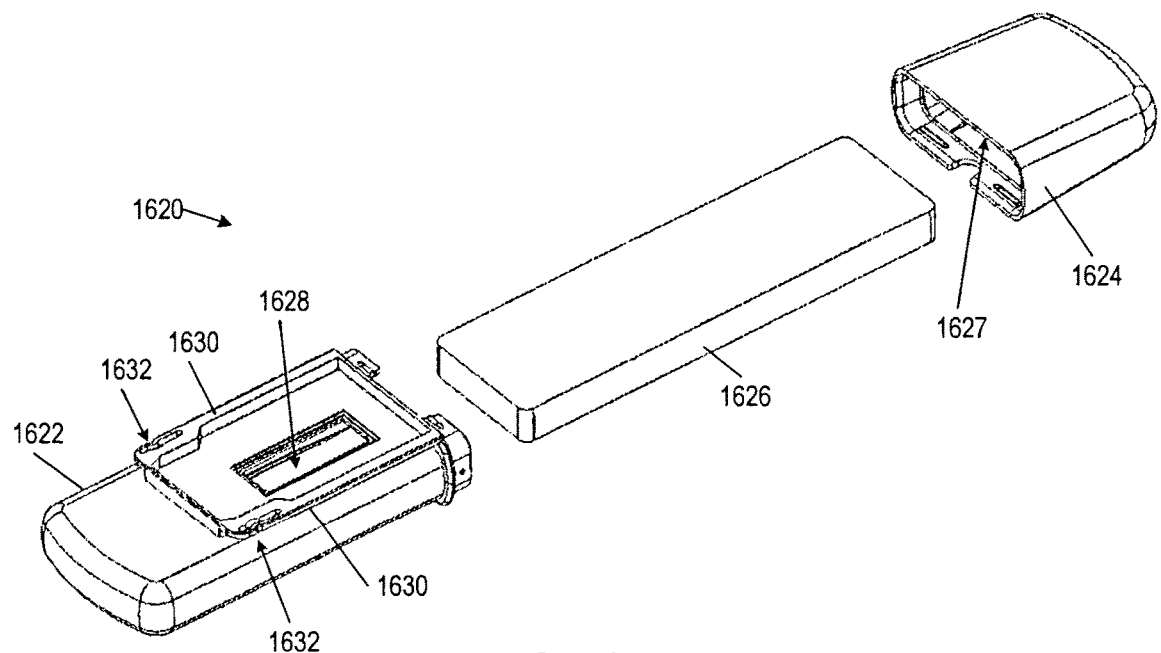

FIGS. 16-1 and 16-2 show an exploded view of test strip adapter 1506 in some examples of the present disclosure. Test strip adapter 1506 includes a test strip cover 1602 and an adapter cap 1604. Test strip cover 1602 is a mechanical attachment to test strip 1508 of a particular type. Test strip cover 1602 defines an opening dimensioned to receive and locks to test strip 1508 by interference fit. Test strip cover 1602 has a top that defines a sample hole 1608. Test strip cover 1602 has tabs 1606 along at least two sides. Tabs 1606 are interlocks shared with test strip adapters for other test strip types so they are all compatible with coupler 1504. Each tab 1606 has a retention feature 1607, such as a detent notch or a detent catch. Adapter cap 1604 fits on and locks to the test strip cover 1602 via retention features (e.g., snap-fit joints). Adapter cap 1604 has a top that defines a sample collector 1610 in communication with sample hole 1608 and a sample port 1612 on test strip 1508.

Figures 1, 17:
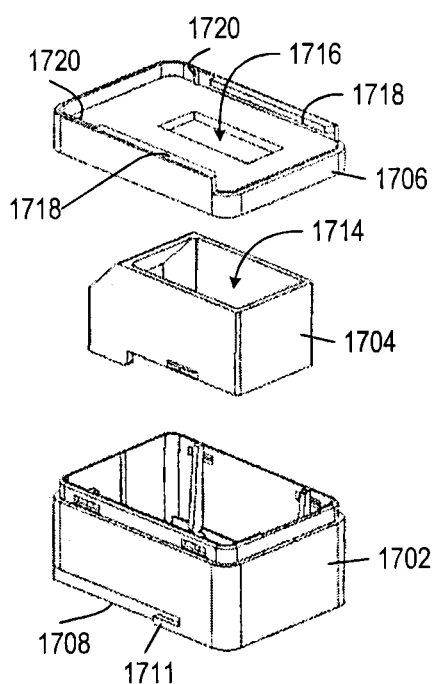
Figures 2, 17:
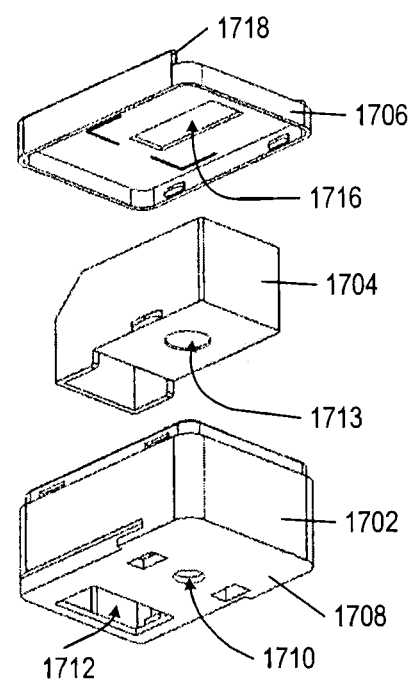

FIGS. 17-1 and 17-2 show an exploded view of coupler 1504 in some examples of the present disclosure. Coupler 1504 is similar to coupler 804 (FIG. 8). Coupler 1504 includes a coupler body 1702, a light guide 1704, and a lid 1706. Coupler body 1702 has a base 1708 that defines a camera window 1710 and a screen window 1712. When coupler 1504 is mounted on clip 1502, camera window 1710 is located over camera window 208 (FIG. 2) and camera 108 (FIG. 1), and screen window 908 is located over screen opening 210 (FIG. 2) and a portion of screen 110 (FIG. 1). Coupler body 1702 has an interlock 1711 on two lower lateral edges that forms a mating pair with a corresponding interlock on clip 1502. For example, interlock 1711 consists of tabs or way, and the counterpart interlock on clip 1502 consists of slots or rails (e.g., slots 706 on clip 700) that receive the tabs or way. Each tab 1711 may include a retention feature (e.g., a detent catch or detent notch) that engages a counterpart retention feature in a corresponding slot on phone adapter 1502.

Light guide 1704 is seated in and affixed to coupler body 1702 by adhesive or mechanical attachment. Light guide 1704 has a space 1714 and a base that defines a hole 1713 over camera window 906 of coupler body 1702. Lid 1706 locks onto the open top of coupler body 1702 to form a casing. Lid 1706 defines a test strip opening 1716 located over hole or space 1714 of light guide 1704.

Lid 1706 has an interlock 1718 on two upper lateral edges that forms a mating pair with a corresponding interlock of test strip adapter 1506. For example, interlock 1718 consists of slots or rails, and the counterpart interlock on test strip adapter 1506 consists of tabs 1606 or way. Each slot 1718 includes a retention feature 1720 that engages a counterpart retention feature in a corresponding tab 1606 of test strip adapter 1506. For example, retention feature 1720 is a detent catch or detent notch.

FIG. 16-3 shows an exploded view of a test strip adapter 1620 in some examples of the present disclosure. Test strip adapter 1620 is compatible with coupler 1504 (FIG. 15). Test strip adapter 1620 includes a sheath 1622 and a cap 1624. Cap 1624 is a mechanical attachment to a test strip 1626 of a particular type. Cap 1624 defines a cavity 1627 that is dimensioned to retain test strip 1626 by interference fit when the test strip inserts into the cap. Test strip 1626 is inserted into sheath 1622 and secured when cap 1624 locks onto the open end of the sheath. Prior to inserting test strip 1626 into sheath 1622, a user deposits a sample on the test strip. The bottom of sheath 1622 defines a test strip opening 1628 to view test strip 1626. Sheath 1622 has tabs 1630 along at least two sides. Tabs 1630 are interlocks shared with test strip adapters for other test strip types so they are all compatible with coupler 1504. Each tab 1630 has a retention feature 1632, such as a detent notch or a detent catch.

Figure 18:
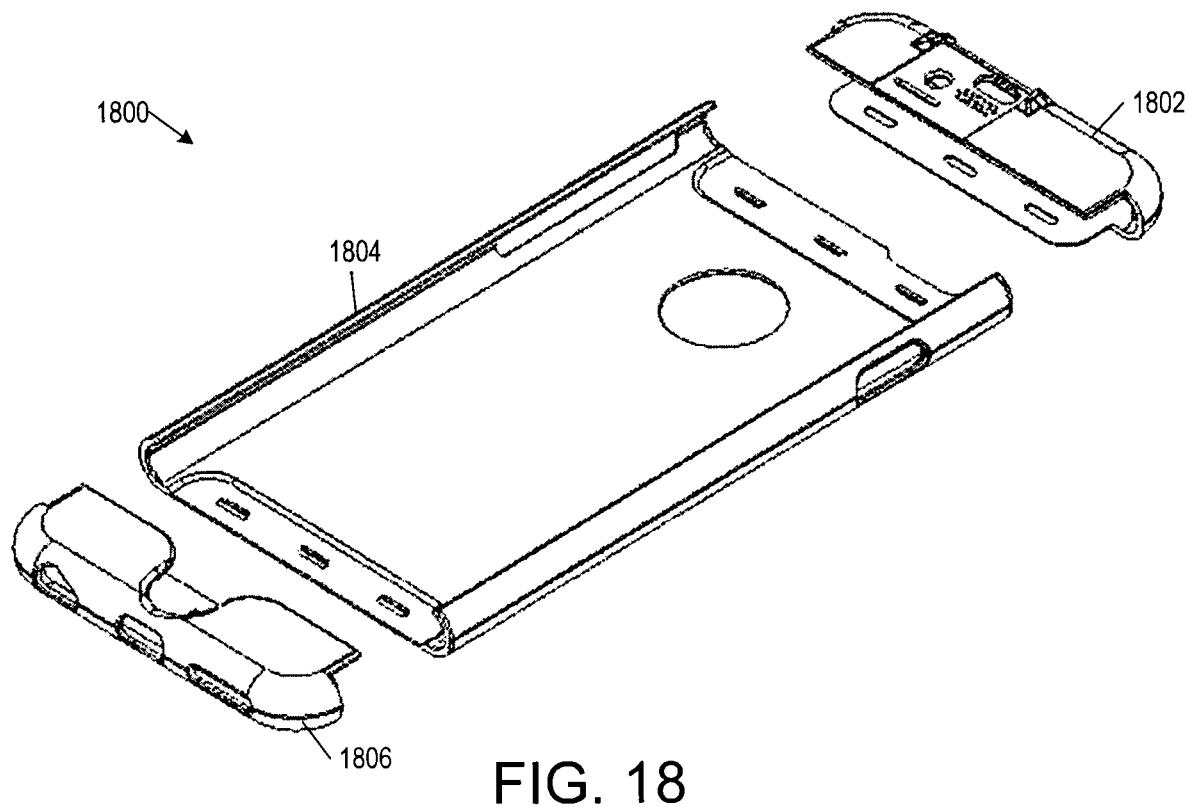
FIG. 18 shows a mobile device case including a phone adapter for a test strip in examples of the present disclosure.

FIG. 18 shows a mobile phone case 1800 in some examples of the present disclosure. Case 1800 includes an upper section 1802, a midsection 1804, and a lower section 1806. Upper section 1802 is implemented similar to the removable clips described in the present disclosure.

Figure 19:
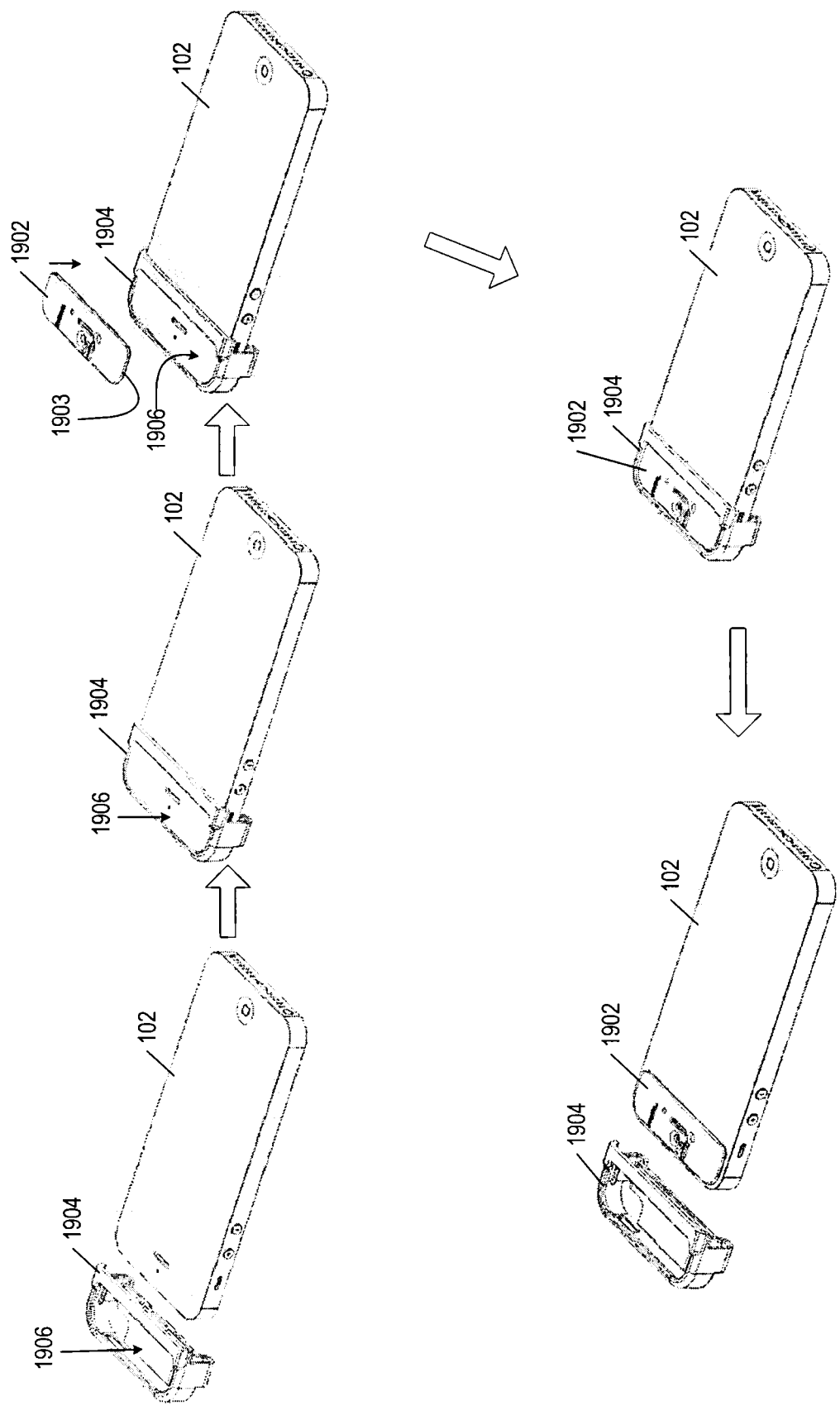
FIG. 19 shows an adhesive-backed phone adapter in examples of the present disclosure.

FIG. 19 shows attaching an adhesive backed phone adapter 1902 to mobile phone 102 in some examples of the present disclosure. Phone adapter 1902 is implemented similar to the faceplates described in the present disclosure. The backside of phone adapter 1902 includes an adhesive tape 1903.

An alignment clip 1904 slides on and secures to the top of mobile phone 102. Alignment clip 1904 defines a mounting space 1906 for phone adapter 1902. The liner to adhesive tape 1903 on the back of phone adapter 1902 is removed, thereby exposing an adhesive. Phone adapter 1902 is then placed in mounting space 1906. After phone adapter 1902 adheres to mobile phone 102, alignment clip 1904 is removed from the mobile phone.

Figure 20:
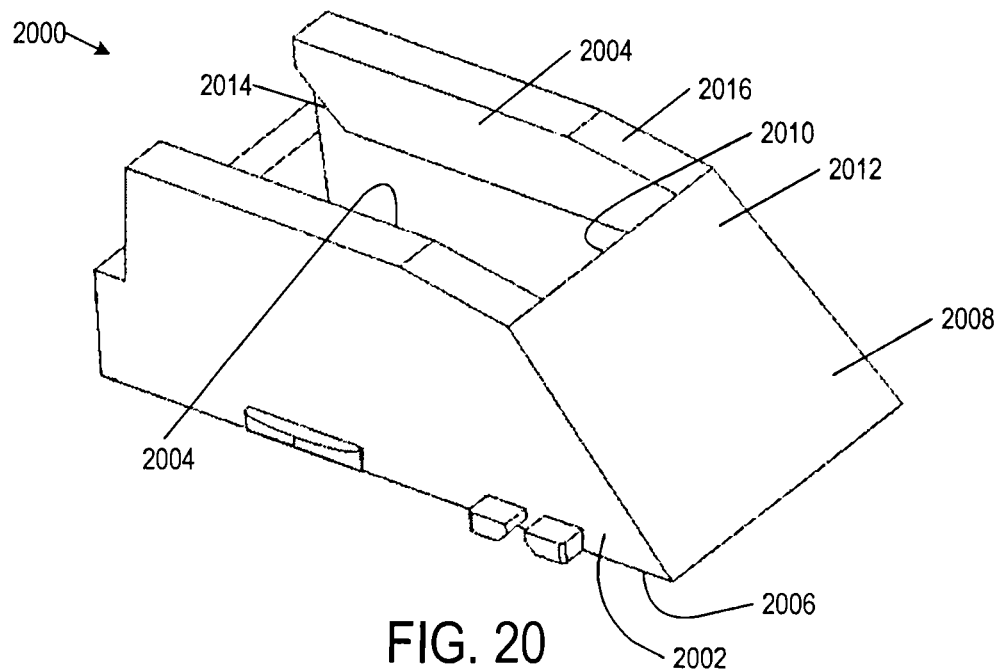
FIGS. 20, 21, and 22 show perspective, side, and top view of a light guide in examples of the present disclosure.
Figure 21:
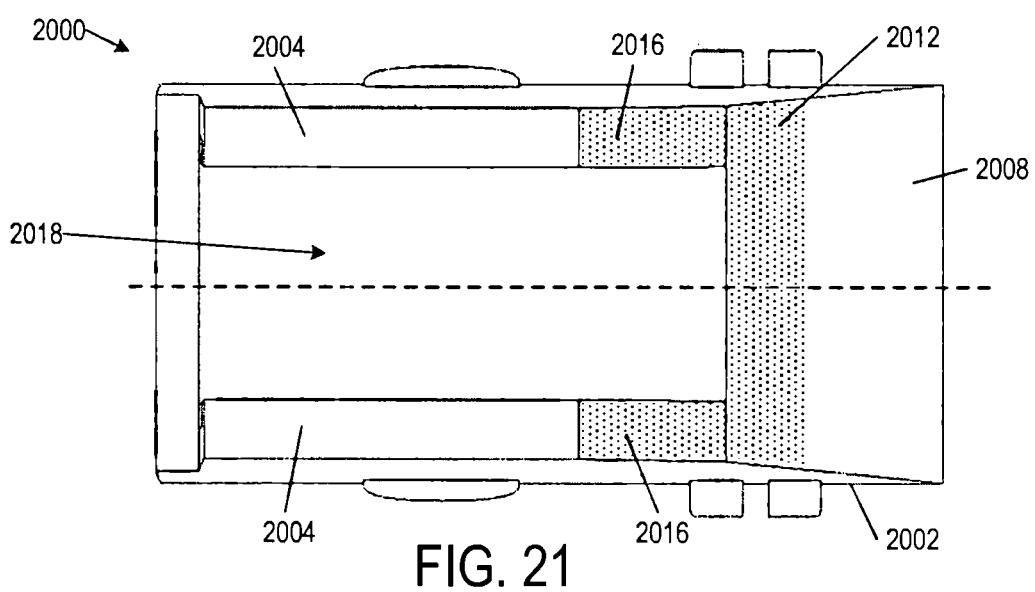
Figure 22:
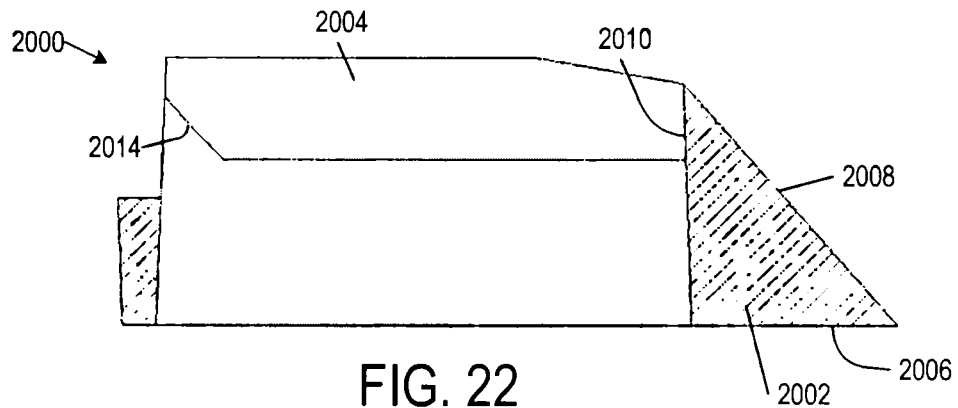

FIGS. 20, 21, and 22 show various views of a light guide 2000 in some examples of the present disclosure. Light guide 2000 may be used as the light guides in the test strip carriers and the couplers described in the present disclosure.

Light guide 2000 has a wedge portion 2002 and leg portions 2004 separated by a space between them. Wedge portion 2002 has a horizontal input surface 2006, an angled reflective surface 2008 above the input surface, and a vertical output surface 2010 opposite the reflective surface. Using total internal reflection, reflective surface 2008 directs light from input surface 2006 to output surface 2010.

Leg portions 2004 extend laterally from output surface 2010 about the top of the output surface opposite. Light enters leg portions 2004, reflects internally, and exit through the top of the leg portions to illuminate an area above the leg portions. Each leg portion 2004 has distal end with a 45° reflective surface 2014. Using total internal reflection, 45° reflective surfaces 2014 directs light out through the top of leg portions 2004.

Angled reflective surface 2008 has a diffusive area 2012 about the top of the angled reflective surface. Diffusive area 2012 helps to scatter the light as it enters leg portions 2004 so the light exits uniformly from the top of leg portions 2004. Each leg portion 2004 includes a diffusive area 2016 on the top of the leg portion near output surface 2010. Diffusive areas 2016 help to scatter the light as it exits that part of leg portions 2004 so the light uniformly illuminate a test strip above the leg portions. A space 2018 is defined between leg portions 2004 to view the test strip.

Figure 23:
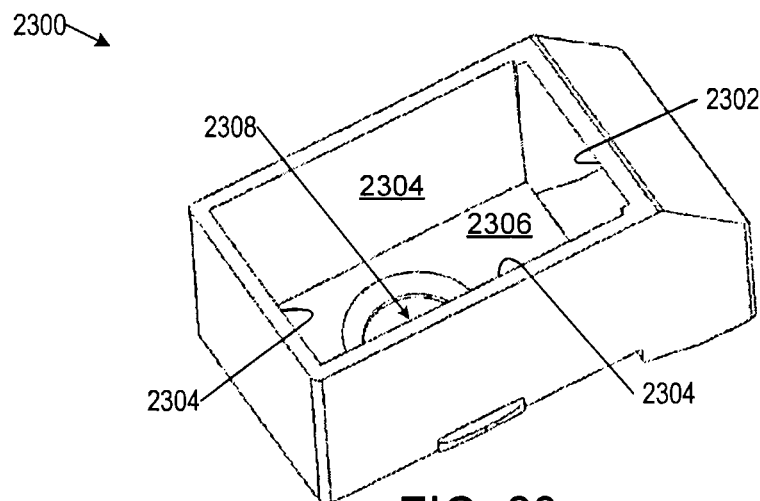
FIGS. 23, 24, and 25 show perspective, side, and top view of another light guide in examples of the present disclosure.
Figure 24:
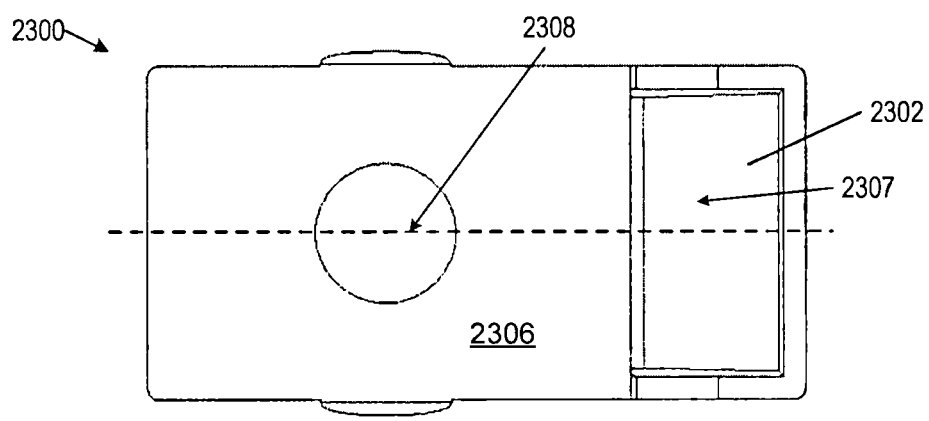
Figure 25:
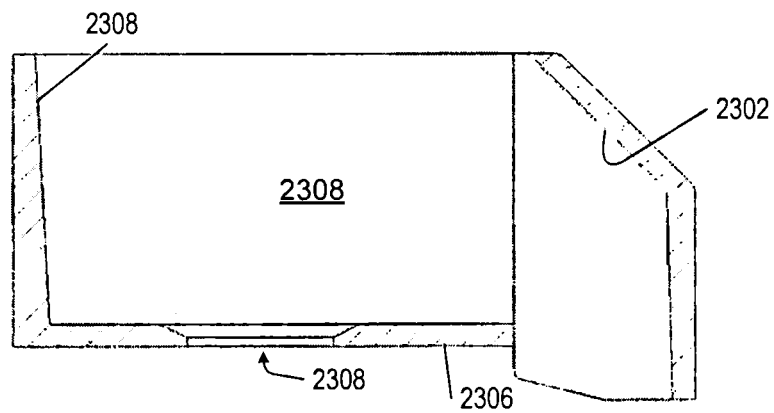

FIGS. 23, 24, and 25 show various views of a light guide 2300 in some examples of the present disclosure. Light guide 2300 may be used as the light guides described in the present disclosure.

Light guide 2300 includes a 45° reflective surface 2302, three reflective sidewall surfaces 2304 defining a space between them, and a reflective base surface 2306. Reflective base surface 2306 defines an input port 2307 that allows light to enter into light guide 2300 from below. Reflective base surface defines a camera window 2308.

Figure 26:
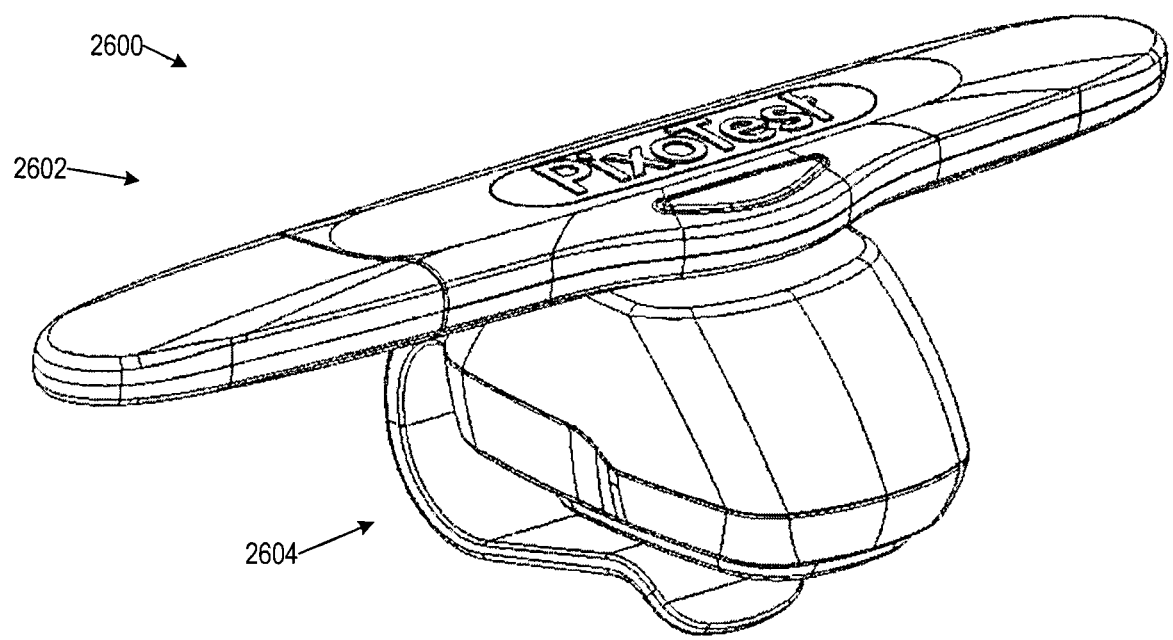
FIG. 26 shows a mobile device accessory in examples of the present disclosure.

FIG. 26 shows an accessory 2600 for a mobile device 102 (e.g., mobile phone) in some examples of the present disclosure. Using accessory 2600 and software, mobile phone 102 is able to measure a characteristic of a test strip and correlate the characteristic to health information. Accessory 2600 includes a test strip adapter 2602 and a universal phone adapter 2604.

Figure 27:
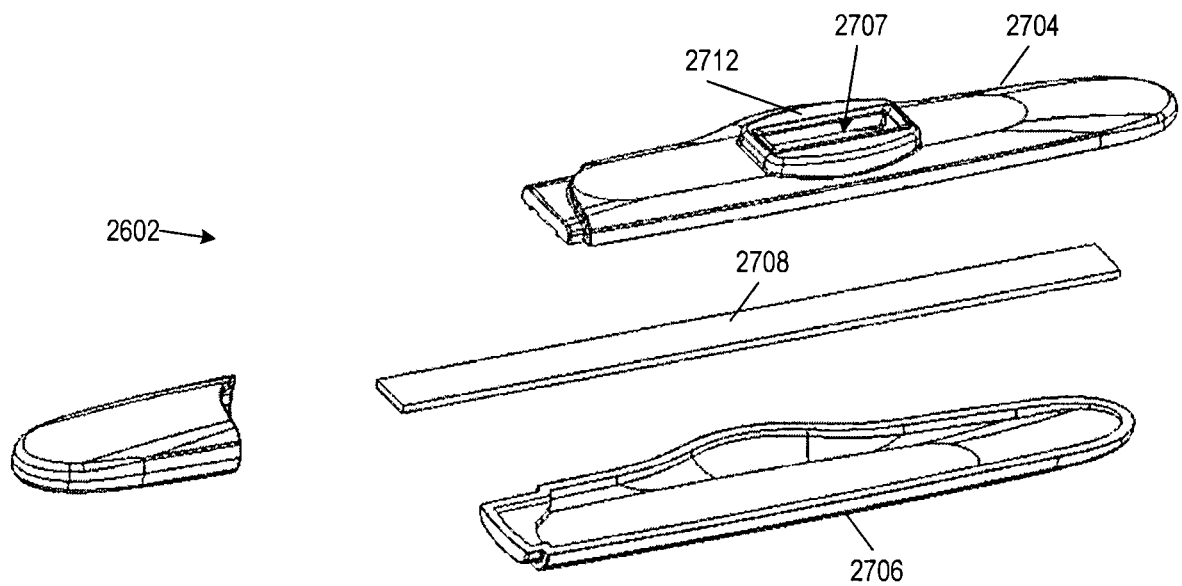
FIG. 27 shows the details of a test strip of FIG. 26 in examples of the present disclosure.

Referring to FIG. 27, test strip adapter 2602 includes a sheath having an upper part 2704 and a lower part 2706. A test strip 2708 is seated and affixed to lower part 2706, and upper part 2704 locks onto the lower part. The bottom of lower part 2706 defines a test strip opening 2707 to view test strip 2708. Lower part 2706 has an insert 2712 that inserts into and frictionally locks to a port 2808 (FIG. 28) of universal phone adapter 2604 (FIG. 28).

Figure 28:
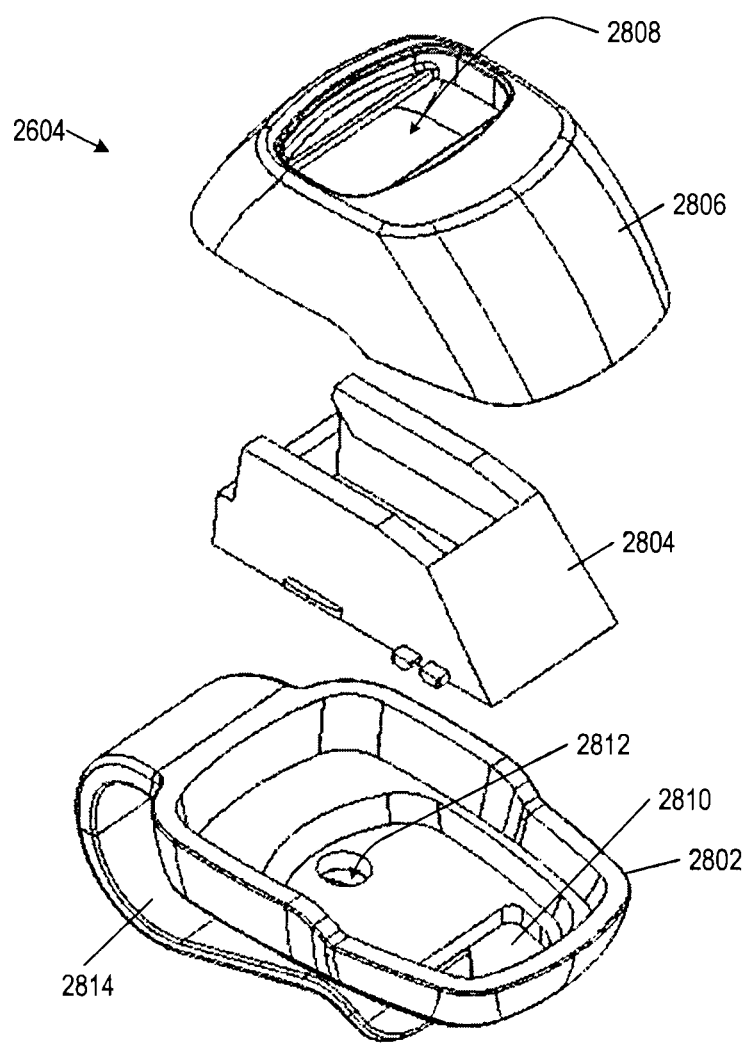
FIG. 28 shows the details of a phone adapter of FIG. 26 in examples of the present disclosure.

Referring to FIG. 28, universal phone adapter 2604 includes an adapter base 2802, a light guide 2804, and an adapter lid 2806. Adapter base 2802 defines a light port 2810 that is located over a portion of screen 110 (FIG. 1) of mobile phone 102. Adapter base 2802 also defines a camera hole 2812 over camera 108 (FIG. 1) of mobile phone 102. Adapter base 2802 includes a universal clip 2814 to secure universal phone adapter 2604 to the top end of mobile phone 102. Universal clip 2814 is dimensioned to fit over and secure to multiple mobile phone models.

Light guide 2804 may be one of the light guides described in the present disclosure. Light guide 2804 is seated in and affixed to adapter base 2802. Adapter lid 2806 defines port 2808 that receives insert 2712 (FIG. 27) of test strip adapter 2602 (FIG. 27). Adapter lid 2806 locks onto adapter base 2802.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

We claim:

1. An accessory for a mobile device to measure characteristics of a test strip, the accessory comprising:
   a test strip adapter comprising a test strip attachment for a test strip type, a first interlock shared with other test strip adapters for other test strip types, and a test strip carrier including a top half defining a sample collector and a bottom half defining a test strip opening to the test strip;
   a phone adapter comprising a phone attachment for a mobile device model and a second interlock shared with other phone adapters for other mobile device models; and
   a coupler, comprising:
      a third interlock that forms a first mating pair with the first interlock of the test strip adapter;
      a fourth interlock that forms a second mating pair with the second interlock of the phone adapter; and
      a light guide having an input surface, wherein the coupler defines a screen opening to a portion of a screen of the mobile device and the input surface is aligned over the screen opening.

2. The accessory of claim 1, wherein the coupler includes a casing comprising:
   an upper portion comprising the third interlock and defining a test strip opening to the test strip in the test strip adapter; and
   a lower portion comprising the fourth interlock and defining a camera opening to a camera of the mobile device.

3. The accessory of claim 2, wherein the light guide is in the casing to receive light received from the portion of the screen from the screen opening and uniformly light the test strip viewed through the test strip opening.

4. The accessory of claim 3, wherein the light guide comprises a wedge portion and two leg portions extending longitudinally from an output face of the wedge portion.

5. The accessory of claim 4, wherein the wedge portion comprises:
   an angled reflective surface above the screen opening;
   a vertical output surface opposite of the angled reflective surface; and
   two leg portions comprise distal ends comprising reflective surfaces.

6. The accessory of claim 5, wherein:
   the angled reflective surface comprises a diffusive area;
   the two leg portions extend from the output surface opposite the diffusive area; and
   the two leg portions have top surfaces comprising the diffusive area proximate to the output surface.

7. The accessory of claim 3, wherein the light guide comprises:
   an angled reflective surface above the screen opening;
   three reflective sidewall surfaces; and
   a base reflective surface defining an opening.

8. The accessory of claim 1, wherein the test strip adapter includes a cover to the coupler, and the cover defines a slot to receive the test strip carrier.

9. The accessory of claim 8, wherein the cover comprises a top sliding door to access the test strip.

10. The accessory of claim 9, wherein the cover comprises a code slot to receive a code card, the code card comprising identifying information about the test strip.

11. A coupler in an accessory to a mobile device for measuring characteristics of a test strip, the coupler including a casing comprising:
   an upper portion comprising a first interlock and defining a test strip opening to the test strip; and
   a lower portion comprising a second interlock and defining (1) a screen opening to a portion of a screen of the mobile device and (2) a camera opening to a camera of the mobile device, the camera opening being opposite of the test strip opening, wherein the coupler further includes a light guide having an input surface aligned over the screen opening and the light guide includes a diffusive area.

12. The coupler of claim 11, wherein the light guide is in the casing.

13. The coupler of claim 12, wherein the light guide comprises a wedge portion and two leg portions extending longitudinally from an output face of the wedge portion.

14. The coupler of claim 13, wherein the wedge portion comprises:
   an angled reflective surface above the screen opening;
   a vertical output surface opposite of the angled reflective surface; and
   two leg portions comprise distal ends comprising reflective surfaces.

15. The coupler of claim 14, wherein:
   the angled reflective surface comprises the diffusive area;
   the two leg portions extend from the output surface opposite the diffusive area; and
   the two leg portions have top surfaces comprising the diffusive area proximate to the output surface.

16. The coupler of claim 11, wherein the light guide comprises:
   an angled reflective surface above the screen opening;
   three reflective sidewall surfaces; and
   a base reflective surface defining an opening.

17. The coupler of claim 11, further comprising a temperature card indicating a temperature.

18. The accessory of claim 1, wherein the coupler comprises a light path, a screen opening to a portion of a screen of the mobile device, a camera opening to a camera of the mobile device, a light filter, and a light guide.

19. The accessory of claim 1, wherein light transmitted from a portion of a screen of the mobile device passes through an opening of a test strip cover to fit onto the test strip and a light filter and reaches a camera of the mobile device.

20. The accessory of claim 1, wherein the phone adapter defines a camera opening on a light path for light transmitted from a portion of a screen of the mobile device through a light filter.

21. An accessory for a computing device to measure characteristics of a test strip, the accessory comprising:
   a test strip adapter comprising a test strip attachment for a test strip type, and a first interlock shared with other test strip adapters for other test strip types, and a test strip carrier including a top half defining a sample collector and a bottom half defining a test strip opening to the test strip; and
   a coupler, coupled to the computing device, comprising:
      a second interlock that forms a first mating pair with the first interlock of the test strip adapter; and
      a light guide having an input surface, wherein the coupler defines a screen opening to a portion of a screen of the computing device and the input surface is aligned over the screen opening.

22. A device to measure characteristics of a test strip, the device comprising:
   a computing device with a display;
   a test strip adapter comprising a test strip attachment for a test strip type, and a first interlock shared with other test strip adapters for other test strip types, and a test strip carrier including a top half defining a sample collector and a bottom half defining a test strip opening to the test strip; and
   a coupler, coupled to the computing device, comprising:
      a second interlock that forms a first mating pair with the first interlock of the test strip adapter; and
      a light guide having an input surface, wherein the coupler defines a screen opening to a portion of the display and the input surface is aligned over the screen opening.

* * * * *